(12) United States Patent
Skatter et al.

(10) Patent No.: US 6,922,460 B2
(45) Date of Patent: Jul. 26, 2005

(54) EXPLOSIVES DETECTION SYSTEM USING COMPUTED TOMOGRAPHY (CT) AND QUADRUPOLE RESONANCE (QR) SENSORS

(75) Inventors: Sondre Skatter, Oakland, CA (US); Timothy James Rayner, San Diego, CA (US); Todor Richard Petrov, Santee, CA (US); Keith Alan Clark, La Mesa, CA (US); Sauveur Chemouni, San Francisco, CA (US); Kenneth Mann, Caterham (GB)

(73) Assignee: Quantum Magnetics, Inc., San Diego, CA (US)

( * ) Notice: Subject to any disclaimer, the term of this patent is extended or adjusted under 35 U.S.C. 154(b) by 98 days.

(21) Appl. No.: 10/460,144

(22) Filed: Jun. 11, 2003

(65) Prior Publication Data

US 2004/0252807 A1 Dec. 16, 2004

(51) Int. Cl.[7] .............................................. G01N 23/04
(52) U.S. Cl. ........................................ 378/57; 378/63
(58) Field of Search .......................... 378/4, 57, 62, 378/63

(56) References Cited

U.S. PATENT DOCUMENTS

| | | | |
|---|---|---|---|
| 5,182,764 A | 1/1993 | Peschmann et al. | 378/57 |
| 5,457,385 A * | 10/1995 | Sydney et al. | 324/301 |
| 5,491,414 A * | 2/1996 | Smith et al. | 324/307 |
| 5,583,437 A * | 12/1996 | Smith et al. | 324/307 |
| 5,642,393 A | 6/1997 | Krug et al. | 378/57 |
| 5,850,625 A | 12/1998 | Maren et al. | 702/93 |
| 6,026,135 A | 2/2000 | McFee et al. | 376/159 |
| 6,067,366 A | 5/2000 | Simanovsky et al. | 382/100 |
| 6,088,423 A * | 7/2000 | Krug et al. | 378/57 |
| 6,111,974 A | 8/2000 | Hiraoglu et al. | 382/100 |
| 6,128,365 A | 10/2000 | Bechwati et al. | 378/57 |
| 6,570,956 B1 * | 5/2003 | Rhee et al. | 378/57 |

OTHER PUBLICATIONS

Tim Rayner et al., "Threat Vector Solutions," Nov. 2001, USA.

N.E.L. Shanks, "Breakthrough in Signal Process Analysis Results in an Operationally Viable 'Certification Plus' NQR Bulk Detection Scanner," Nov. 2001, USA.

Alex Hudson et al., "Quadrupole Resonance (QR): State of the Art," Nov. 2001, USA.

* cited by examiner

*Primary Examiner*—David V. Bruce
*Assistant Examiner*—Courtney Thomas
(74) *Attorney, Agent, or Firm*—Cantor Colburn LLP

(57) ABSTRACT

An explosives detection system which includes computed tomography (CT) and quadrupole resonance (QR) sensors for identifying particular explosive compounds present in passenger baggage. The CT sensor may be configured to automatically identify the presence or absence of bulk military, commercial, and sheet explosives during CT scanning of the baggage. Similarly, the QR sensor may be configured to responsively generate RDX and PETN signals during QR scanning of the passenger baggage. Using any of a variety of inspection protocols, the explosives detection system may generate an output alarm based upon data obtained from the CT and QR sensors.

87 Claims, 13 Drawing Sheets

| Output of the QR and CT Sensor Systems of the Baggage Inspection System ||| 
|---|---|---|
| Detectors | Possible Output Values | Sensor System |
| Sheet | Alarm/Clear | Computed Tomography (CT) |
| Military (bulk) | Alarm/Clear | Computed Tomography (CT) |
| Commercial | Alarm/Clear | Computed Tomography (CT) |
| RDX Signals | Continuous (Real Numbers) | Quadrupole Resonance (QR) |
| PETN Signals | Continuous (Real Numbers) | Quadrupole Resonance (QR) |
| QR Shield | Alarm/Clear | Quadrupole Resonance (QR) |
| CT Shield | Alarm/Clear | Computed Tomography (CT) |

FIG. 2

| Alarm Category | Computed Tomography (CT) Screening | Quadrupole Resonance (QR) Screening | Inspection System Output |
|---|---|---|---|
| Bulk Military | Alarm | -------- | Alarm |
|  | Alarm | -------- | Alarm |
|  | Clear | -------- | Clear |
|  | Clear | -------- | Clear |
| Sheet | Alarm | RDX, PETN, or QR Shield | Alarm |
|  | Alarm | No RDX, PETN, or QR Shield | Clear |
|  | Clear | -------- | Clear |
|  | Clear | -------- | Clear |
| Commercial | Alarm | -------- | Alarm |
|  | Alarm | -------- | Alarm |
|  | Clear | -------- | Clear |
|  | Clear | -------- | Clear |
| CT Shield | Alarm | -------- | Alarm |
|  | Alarm | -------- | Alarm |
|  | Clear | -------- | Clear |
|  | Clear | -------- | Clear |

Truth Table for CT and QR Screening Systems (Mode 1 Operation)

FIG. 4

| Truth Table for CT and QR Screening Systems |||||
|---|---|---|---|
| (Mode 2 Operation) |||||
| Alarm Category | Computed Tomography (CT) Screening | Quadrupole Resonance (QR) Screening | Inspection System Output |
| Bulk Military | Alarm | --------- | Alarm |
| | Alarm | --------- | Alarm |
| | Clear | --------- | Clear |
| | Clear | --------- | Clear |
| Sheet | Alarm | RDX, PETN, or QR Shield | Alarm |
| | Alarm | No RDX, PETN, or QR Shield | Clear |
| | Clear | RDX, PETN, or QR Shield | Clear |
| | Clear | No RDX, PETN, or QR Shield | Clear |
| Commercial | Alarm | --------- | Alarm |
| | Alarm | --------- | Alarm |
| | Clear | --------- | Clear |
| | Clear | --------- | Clear |
| CT Shield | Alarm | --------- | Alarm |
| | Alarm | --------- | Alarm |
| | Clear | --------- | Clear |
| | Clear | --------- | Clear |

FIG. 6

| Truth Table for CT and QR Screening Systems |||||
|---|---|---|---|
| (Mode 3 Operation) |||||
| Alarm Category | Computed Tomography (CT) Screening | Quadrupole Resonance (QR) Screening | Inspection System Output |
| Bulk Military | Alarm | -------- | Alarm |
| | Alarm | -------- | Alarm |
| | Clear | -------- | Clear |
| | Clear | -------- | Clear |
| Sheet | -------- | RDX, PETN, or QR Shield | Alarm |
| | -------- | No RDX, PETN, or QR Shield | Clear |
| | -------- | RDX, PETN, or QR Shield | Alarm |
| | -------- | No RDX, PETN, or QR Shield | Clear |
| Commercial | Alarm | -------- | Alarm |
| | Alarm | -------- | Alarm |
| | Clear | -------- | Clear |
| | Clear | -------- | Clear |
| CT Shield | Alarm | -------- | Alarm |
| | Alarm | -------- | Alarm |
| | Clear | -------- | Clear |
| | Clear | -------- | Clear |

FIG. 8

| Logical Truth Table for CT and QR Screening Systems (Mode 4 Operation) ||||
|---|---|---|---|
| Alarm Category | Computed Tomography (CT) Screening | Quadrupole Resonance (QR) Screening | Inspection System Output |
| Bulk Military | Alarm | Alarm/Clear/Indet. | Alarm |
| | Clear | Alarm | Alarm |
| | Clear | Clear/Indet. | Clear |
| Sheet | Alarm | Alarm/Indet./QR Shield | Alarm |
| | Alarm | Clear | Clear |
| | Clear | Clear/Indet./QR Shield | Clear |
| | Clear | Alarm | Alarm |
| Commercial | Alarm | -------- | Alarm |
| | Clear | -------- | Clear |
| CT Shield | Alarm | -------- | Alarm |
| | Clear | -------- | Clear |

FIG. 10

EXPLOSIVES DETECTION SYSTEM USING COMPUTED TOMOGRAPHY (CT) AND QUADRUPOLE RESONANCE (QR) SENSORS

BACKGROUND OF THE INVENTION

1. Field of the Invention

The present invention relates generally to an inspection system, and in particular to a baggage inspection system for detecting explosives using computed tomography (CT) and quadrupole resonance (QR) sensors.

2. Discussion of the Related Art

Over the years, baggage inspection systems have evolved from simple X-ray imaging systems that were completely dependent on interpretation by an operator to more sophisticated systems that can automatically recognize certain types of contraband. Some systems employ single energy or dual energy X-ray radiation transmitted through or scattered from examined baggage. Some systems use a single view detector arrangement, while other systems utilize dual-view or multi-view arrangements. Single or dual-view systems usually scan baggage as it moves on a conveyor using a fan beam or a scanning pencil beam of X-rays in a fixed geometry. Multi-view CT sensors, on the other hand, usually scan stationary or moving baggage in a fixed geometry of scan angles and process data corresponding to the absorption of X-rays to reconstruct selected slices of the baggage.

In general, performance of explosives detection systems is measured using three primary parameters: false alarm rate, probability of detection, and scanning speed (throughput). Often, the improvement of one parameter is at the expense of the other parameters. For example, an increase in throughput may result in the undesirable effect of an increased false alarm rate or reduced probability of detection.

Although many CT based systems exhibit an excellent probability of detection, these systems are susceptible to high false alarm rates. A common reason for the generation of a false alarm is that conventional CT sensors have difficulty in distinguishing actual threat objects from harmless objects since these objects may exhibit similar threat definitions (for example, similar density and mass). Although there has been continued effort to improve false alarm rates of explosives detection systems employing CT technologies, for example, improvement is still needed.

SUMMARY OF THE INVENTION

The explosives detection system of the present invention includes CT and QR sensors for identifying particular explosive compounds present in passenger baggage. The CT sensor may be configured to automatically identify the presence or absence of military, plastic, powder, commercial, and sheet explosives during CT scanning of the baggage. Similarly, the QR sensor may be configured to responsively generate QR signals from explosives, such as RDX and PETN, during QR scanning of the passenger baggage. Using any of a variety of inspection protocols, the explosives detection system may generate an output alarm based upon data obtained from the CT and QR sensors.

In accordance with one aspect of the present invention, the CT sensor may be replaced with automated sensors such as an X-ray sensor, single-view X-ray sensor, or a multi-view X-ray sensor.

In accordance with another aspect of the present invention, the QR and CT sensors, which will be collectively referred to herein as a QRCT scanning system, may be integrated into a single baggage inspection system (which may contain other sensors such as an X-ray diffraction sensor), or the QR and CT sensors may be configured as individual, standalone sensor units.

In another aspect of the present invention, the QR and CT sensors may each be further adapted to automatically generate alarm signals to respectively identify QR and CT shielding present in the baggage. In this configuration, the QR or CT sensors, or both, may be configured with a separate shield sensor to respectively identify QR or CT shielding.

BRIEF DESCRIPTION OF THE DRAWING

The above and other aspects, features and advantages of the present invention will become more apparent upon consideration of the following description of preferred embodiments taken in conjunction with the accompanying drawing, wherein:

FIG. 2 is a table showing various detectors that may configured with the CT and QR sensors of FIG. 1;

FIG. 4 is a truth table showing inspection logic for the scanning protocol depicted in FIG. 3;

FIG. 6 is a truth table showing inspection logic for the scanning protocol depicted in FIG. 5;

FIG. 8 is a truth table showing inspection logic for the scanning protocol depicted in FIG. 7;

FIG. 10 is a truth table showing inspection logic that may be used for implementing the three-state scanning protocol depicted in FIG. 9;

DETAILED DESCRIPTION OF THE PREFERRED EMBODIMENTS

In the following description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention.

As a matter of convenience, many embodiments of the invention will be described in the context of a passenger baggage inspection system implemented as part of a typical aviation security system. Particular reference will be made to passenger "baggage" which is screened for explosives and other threat objects. However, it is to be understood that the present invention is not so limited and that many other applications are envisioned and possible within the teachings of this invention. Examples of particular applications of baggage inspection systems that may also be implemented include seaports, public buildings, public transportation facilities, prisons, hospitals, power plants, office buildings, hotels, and casinos, among others. The term "baggage" is used herein to generally define items that may be screened by the baggage inspection system of the present invention and which may contain, or be constructed of, various types of explosive materials. Possible types of baggage items include, for example, passenger baggage, checked baggage, parcels, mail, packages, break bulk cargo, aircraft and marine containers, laptop or portable computers, and the like.

Figure 1:
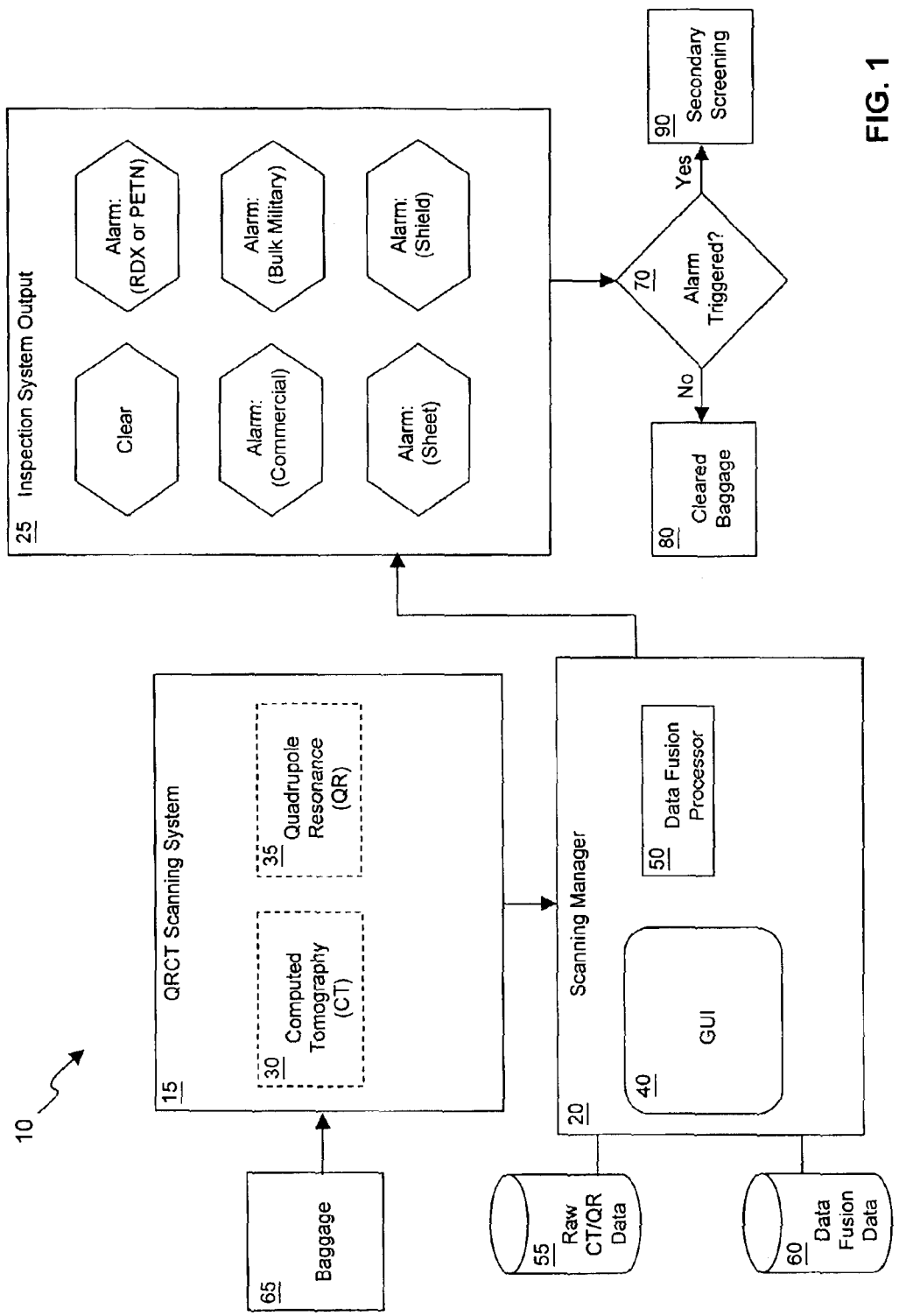
FIG. 1 is a block diagram of one embodiment of a baggage inspection system of the present invention.

Referring now to FIG. 1, a block diagram of one embodiment of a baggage inspection system 10 of the present invention is shown. Inspection system 10 generally includes QRCT scanning system 15, scanning manager 20, and inspection system output unit 25.

In general, the QRCT screening system may be configured with computed tomography (CT) sensor 30 and quadrupole resonance (QR) sensor 35. CT sensor 30 may be implemented using any of a variety of commercially available X-ray CT sensors configured to detect the presence of explosives and other objects of interest in passenger baggage.

CT is a technique that produces a cross-sectional image of an object from a series of attenuation measurements taken from different angles around the object. CT reconstructed data may provide precise, quantitative information about the characteristics of objects in the scan plane. Components of a typical CT sensor include an X-ray source and detector units respectively secured to diametrically opposite sides of an annular-shaped platform or disk. The disk is mounted within a gantry support so that in operation the disk continuously rotates about a rotation axis while X-rays pass from the source through an object positioned within the opening of the disk to the detector system.

In operation, as the disk rotates around the object being scanned, the scanner generates a plurality of projections at a corresponding plurality of projection angles. Using well known algorithms, a CT image of the object may be generated from all the projection data collected at each of the projection angles. The CT image is representative of the mass and density of a two dimensional "slice" of the object through which the fan beam has passed during the rotation of the disk through the various projection angles. Machine vision, for example, may be used to examine each slice to determine the presence or absence of particular types or classifications of explosives using known methods.

In accordance with some embodiments, an appropriately configured CT sensor can detect five primary categories of explosives, generally known in the art as military, plastic, sheet, commercial, and powder explosives. For convenience, the term "bulk military explosives" will be used herein to collectively refer to military and plastic explosives, while the term "commercial explosives" will be used to collectively refer to commercial and powder explosives.

Bulk military explosives may include Semtex, C-4, and TNT, among others. In some instances, bulk military may contain RDX and/or PETN, and/or other explosive materials. Sheet explosives include Semtex, Detasheet, C-4, and other explosive materials that contain RDX and/or PETN, and/or other explosive materials. Commercial explosives define compounds that include Ammonium Nitrate (AN), dynamite, nitroglycerin (NG), emulsions, and the like. Bulk military and commercial explosives are typically characterized on the basis of mass and density, whereas sheet explosives are typically characterized using parameters such as geometry and density (for example, a flattened shape). An example of a suitable CT sensor system that may be modified in accordance with the invention is the CTX 5500 DS explosives detection system developed by InVision Technologies of Newark, Calif.

Although many embodiments will be described with reference to the use of CT technologies, the present invention is not so limited and other types of baggage imaging devices may be used as an alternative to CT-based systems. Suitable bag imaging technologies include, for example, X-ray, magnetic resonance imaging (MRI), automatic X-ray, multi-view X-ray, and the like. Accordingly, CT sensor 30 may alternatively be implemented using almost any technology that can image the contents of baggage to automatically identify explosives within the baggage. The term "X-ray sensor" will be used herein to generally define baggage imaging devices that may be used in accordance with the present invention. For convenience, further description of the present invention will be made with reference to the use of CT technologies, but it is to be understood that the disclosed principles apply equally to other imaging technologies and systems.

QR sensor 35 may be implemented using any of a variety of commercially available sensor systems configured to detect the presence of explosives in passenger baggage using quadrupole resonance (QR). An appropriately configured QR sensor 35 can detect a wide range of explosives such as those containing PETN, RDX, TNT, Tetryl, Ammonium Nitrate (AN), black powder, and the like. If desired, the QR sensor may be easily configured with additional screening capabilities for detecting illegal drugs such as cocaine, heroin, and MDMA, among others. For convenience, further description of the present invention will focus on the QR sensor detecting explosive compounds containing RDX, PETN, or both. However, it is to be understood that the teachings provided herein apply equally to other materials that can be detected using known QR techniques.

If desired, the CT or QR sensors, or both, may be optionally configured with an ability to detect the presence of shielding to supplement their explosives detection capabilities. For example, the CT or QR sensor may trigger a shield alarm whenever the scanned baggage contains material that prevents the sensor system from appropriately interrogating the baggage. Techniques for detecting shielding are well known in the art, and need not be further described.

QR is a branch of radio frequency spectroscopy that has been used for the detection of explosives and drugs. QR exploits the inherent electrical properties of atomic nuclei. Nuclei with non-spherical electric charge distributions possess electric quadrupole moments. In solid materials, electrons and atomic nuclei produce electric field gradients. These electric field gradients interact with the nuclear quadrupole moments of quadrupolar nuclei, producing energy levels for the quadrupolar nuclei, and hence their characteristic transition frequencies. Measurements of these frequencies, or relaxation time constants, or both, can indicate not only which nuclei are present but also their chemical environment.

In operation, using carefully tuned pulses of low intensity electromagnetic waves, a quadrupole resonance device probes the molecular structure of targeted items such as explosives and narcotics. The quadruple resonance momentarily disturbs the alignment of target nuclei within the item scanned. As the nuclei realign themselves, they emit a characteristic signal of their own, which is picked up by a receiver and sent to a computer for rapid analysis. The signal emitted by each type of explosive or illegal drug is unique. Specialized radio frequency pulse sequences have been developed for optimal detection of particular explosives and illegal drugs such as cocaine and heroin. The QScan QR 500 explosives detection system, developed by Quantum Magnetics, Inc., of San Diego, Calif., is one such system that may be modified in accordance with the invention to implement QR sensor 35.

In many embodiments, QR sensor 35 does not require human interpretation or analysis in determining the existence (alarm) or absence (clear) of explosives within passenger baggage. Automated detection is typically obtained by setting a predetermined threshold signal value to trigger an alarm. Specifics regarding the setting of a QR sensor threshold value, and particular implementations of a dual-threshold sensor, will be described in more detail with regard to later figures.

Scanning manager 20 is shown including a graphical user interface (GUI) 40 and a data fusion processor 50. In general, the scanning manager analyzes data captured by the various sensors of QRCT scanning system 15, and presents this data and alarm status, for example, to associated output devices such as a graphical user interface (GUI) and storage devices.

Certain aspects of the data fusion process of the invention can be implemented with a software application written in any suitable programming language. The programming language chosen should be compatible with the computing platform according to which the software application is executed. Examples of suitable programming languages include C and C++.

Data fusion processor 50 may be implemented using any suitable computational device that provides the necessary control, monitoring, and data analysis of the associated sensors and alarms utilized by scanning system 15 and inspection system output unit 25. In general, the data fusion processor contains the necessary inspection logic for generating output alarms based upon threat data generated by CT sensor 30 and QR sensor 35. As will be discussed in detail herein, the inspection system may generate an output alarm based upon data obtained from the CT and QR sensors and processed using a variety of different inspection protocols.

The data fusion processor may be a specific or general purpose computer such as a personal computer having an operating system such as DOS, Windows, OS/2 or Linux; Macintosh computers; computers having JAVA OS as the operating system; graphical workstations such as the computers of Sun Microsystems and Silicon Graphics, and other computers having some version of the UNIX operating system such as AIX or SOLARIS of Sun Microsystems; or any other known and available operating system, or any device including, but not limited to, laptops and hand-held computers.

GUI 40 may be any suitable display device operable with any of the computing devices described herein and may comprise a display device such as an LCD, CRT, plasma monitor, and the like. In many embodiments, the GUI may be implemented as a centralized display device providing data obtained from the CT and QR sensors during a baggage screening process. However, additional display devices may be used, if so desired.

Data that may be displayed on the GUI includes the existence or absence of a detected threat object, the output parameters of inspection system output unit 25 (clear, commercial, bulk military, sheet, RDX or PETN, shield, among others), sensor threshold values (QR and CT), as well as any threat data (mass, volume, number of threats, for example). GUI 40 may also provide a system operator with an ability to control or modify various scanning parameters of the CT and QR sensors.

The communication link between QRCT scanning system 15 and scanning manager 20 may be implemented using any suitable method that supports the transfer of information such as data, video, and image information. In many embodiments, the communication link is implemented using conventional communication technologies such as UTP, Ethernet, coaxial cables, serial or parallel cables, optical fibers, among others. Although the use of wireless communication technologies is possible, they are typically not utilized since they may not provide the necessary level of security required by many applications such as airport baggage screening systems.

In many implementations, scanning manager 20 is physically configured in close physical proximity to the QRCT scanning system. However, some or all of the components of the scanning manager may be remotely implemented relative to the QRCT scanning system. Remote implementations may be accomplished by configuring the QRCT scanning system and the scanning manager with a suitably secure network link that comprises anything from a dedicated connection, to a local area network (LAN), to a wide area network (WAN), to a metropolitan area network (MAN), or even to the Internet.

An example of a remote application may be where the scanning manager and associated GUI display are located at an airport security office, which could be located some distance away from the CT and QR sensors comprising the QRCT baggage scanning system. Examples of distant locations include: across the room; in a different room; in a different building; or at any practical distance. Another implementation may be where the scanning manger is located at a local, regional, or national security office of a particular airport or airline that is responsible for operating the baggage inspection system.

Scanning manager 20 is also shown configured with data storage units 55 and 60. Data storage unit 55 may be used for storing raw data generated by CT and QR sensor 30 and 35 during the screening of baggage. Typical data generated by the CT sensor includes the number of threat objects detected, bag weight, bag dimensions, and the like. For each threat object detected, data such as the type of threat object identified, minimum CT value, maximum CT value, average CT value, mass of the threat object, and volume of the threat object, may also be obtained. Typical data generated by the QR sensor may include peak value, peak frequency, tune value, Q value, and temperature, among others. Data storage 60 may be used to store CT and QR data that has been merged into a suitable format for processing by data fusion processor 50 in accordance with the invention.

Data storage units 55 and 60 may be implemented using any type (or combination) of suitable volatile and non-volatile memory or storage devices including random access memory (RAM), static random access memory (SRAM), electrically erasable programmable read-only memory (EEPROM), erasable programmable read-only memory (EPROM), programmable read-only memory (PROM), read-only memory (ROM), magnetic memory, flash memory, magnetic or optical disk, or other similar memory or data storage means.

A typical baggage inspection process for detecting explosives may proceed as follows. Initially, bag 65 may be introduced to QRCT scanning system 15 so that the baggage may be screened for explosives by CT sensor 30 and QR sensor 35. It is to be understood that the screening sequence may be implemented in several different ways. For example, in some implementations, a bag is first screened by the CT sensor followed by screening by the QR sensor. In other embodiments, the bag is first screened by the QR sensor followed by the CT sensor. In some instances, a bag may be screened using only the QR sensor. With few exceptions, no particular screening order is required.

After screening, regardless of the screening order utilized, the CT and QR sensors may communicate generated threat data to scanning manager 20 for analysis. In accordance with various inspection protocols, data fusion processor 50 processes the threat data to generate an appropriate output. For example, if no alarms have been triggered indicating that the screened baggage item does not contain explosives, a clear signal may be generated and the bag may be directed to a cleared baggage area (blocks 70, 80). On the other hand, if one or more explosives alarms are triggered (commercial, bulk military, etc.), then the suspicious bag may be identified as requiring alarm resolution and submitted to, for example, a secondary screening area for further processing (blocks 70, 90).

The secondary screening area may be implemented as a level two inspection area. In a typical level two inspection area, an operator may visually inspect an X-ray image of the rejected bag and attempt to determine whether a suspicious object inside the bag can be cleared based on its obvious shape. In some instances, the operator may obtain additional CT slice images of the suspicious bag. The operator may search the image for characteristic objects such as weapons, components of an improvised explosive device (IED), or other characteristics associated with explosives and other contraband. The operator at a level two inspection station can typically clear most, but not all, of the rejected bags during this manual threat resolution process.

As will be described in detail herein, the baggage inspection system of the present invention does not merely combine screening results from the CT and QR sensors, but it obtains results using a variety of different screening protocols. As such, the performance of the various embodiments of the invention cannot therefore be deduced by separately considering the performance data of the QR and CT sensors.

FIG. 2 is a table showing various detectors that may configured with the CT and QR sensors 30 and 35, as well as the possible output values of these detectors. The CT sensor is shown having sheet, bulk military, and commercial explosives detectors. These particular detectors may provide an alarm or clear indication to indicate the presence or absence of a particular type of explosive (sheet, bulk military, commercial, for example). The QR sensor, on the other hand, may provide RDX and PETN detection signals. The RDX and PETN signals generated by the QR sensor may be used to implement a two-state or three-state logic inspection protocol. If desired, any of the embodiments of the present invention may include shield detection, which may be implemented as part of the QR sensor, the CT sensor, or both.

Figure 3:
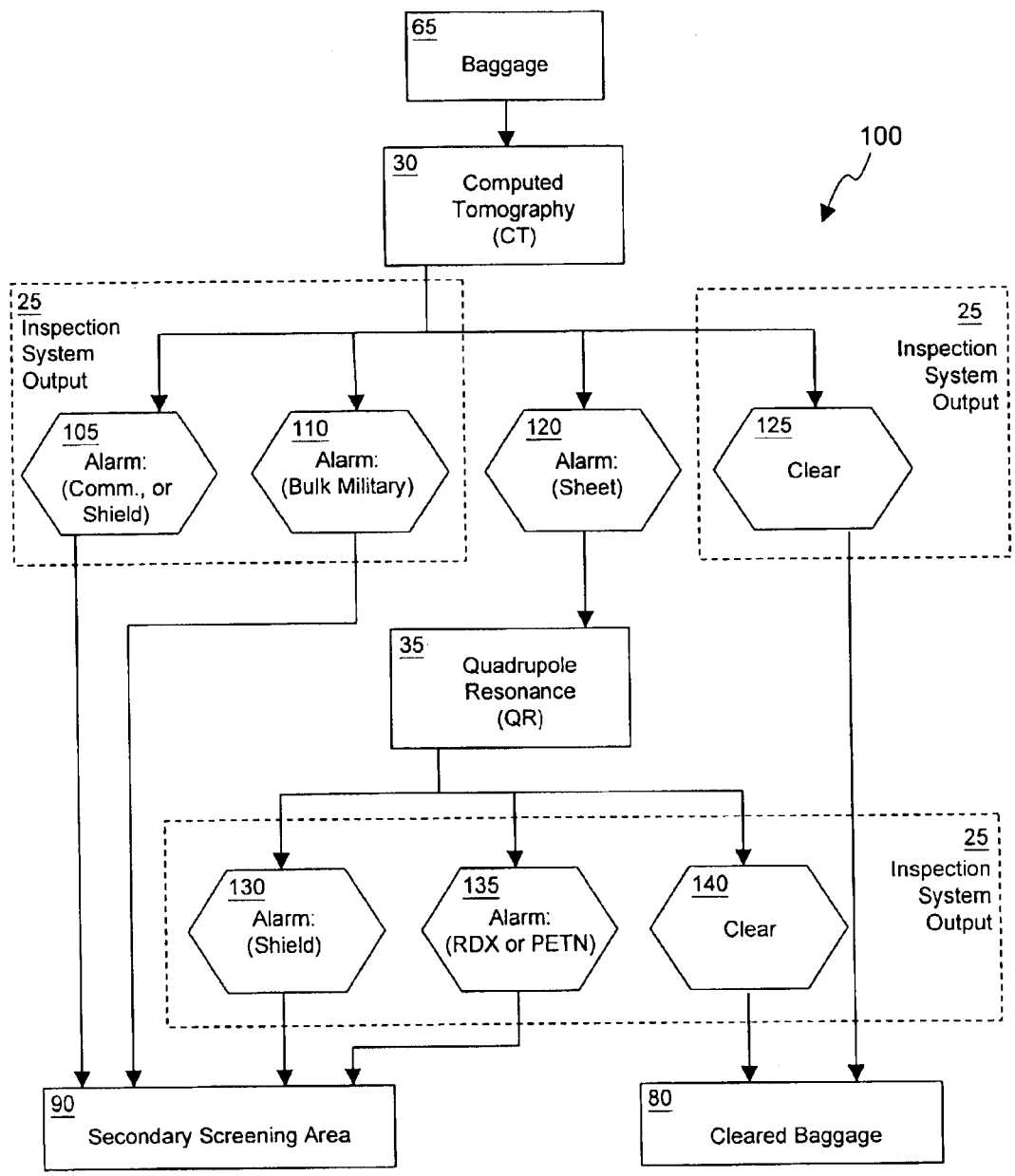
FIG. 3 is a flowchart showing a scanning protocol for implementing a baggage inspection system according to one embodiment of the present invention.

FIG. 3 is a flowchart showing a scanning protocol for implementing a baggage inspection system according to one embodiment of the present invention and will be described with reference to inspection system 10 shown in FIG. 1. In this embodiment, baggage is first screened by CT sensor 30, and if necessary, by QR sensor 35. The depicted configuration shows the CT sensor operating as a primary screening tool, with the QR sensor utilized to resolve a sheet alarm generated by the CT sensor.

In this figure, baggage initially enters the CT sensor where it may undergo a scanning process to determine the presence or absence of explosives using known explosives detection methods (blocks 65, 30). If the CT sensor detects commercial, bulk military, or shielding, the system may generate the appropriate alarms indicating that the bag requires alarm resolution using, for example, secondary screening area (blocks 105, 110, 90). However, if the CT sensor determines that the baggage is free of explosives, a clear indication may be generated and the bag may be directed to the cleared baggage area (blocks 125, 80). In either of these two scenarios, it is not necessary for the bag to be scanned by QR sensor 35.

On the other hand, if the CT sensor detects sheet explosives during initial scanning of the bag, the bag may be directed to the QR sensor so that further scanning may be performed (block 35).

After the QR sensor scans the suspicious bag, an alarm or clear indication may be generated based upon the scan results. If shielding or predetermined threshold levels of RDX or PETN are detected, the system may generate the appropriate alarms and the bag may be directed to the secondary screening area for further processing (blocks 130, 135, 90). However, if the QR sensor does not detect shielding, RDX, or PETN on or within the scanned baggage, it may provide a clear indication so that the baggage may be directed to the cleared baggage area (blocks 140, 80).

In the embodiment depicted in FIG. 3, the QR sensor only scans bags with respect to which the CT sensor has generated a sheet alarm and thus, the QR sensor will typically scan fewer bags than the CT sensor. As such, the role of the QR sensor is to resolve or confirm sheet alarms generated by the CT sensor. If desired, the scan time of the QR sensor may be increased to enhance detection accuracy which, notably, does not affect overall inspection system throughput since the QR sensor is handling fewer bags than the CT sensor. Another alternative may be to utilize one QR sensor to scan baggage received from a plurality of CT sensor systems.

FIG. 4 is a truth table showing inspection logic for the scanning protocol depicted in FIG. 3. The left-hand side of this figure shows the various alarm source categories, while the right-hand column depicts the possible outputs that may be generated by the baggage inspection system utilizing the CT and QR sensor systems.

Bulk military, commercial, and CT shield alarms are essentially determined by the CT sensor outputs. However, in situations where the CT sensor generates a sheet alarm, the output from the QR sensor output is controlling.

Figure 5:
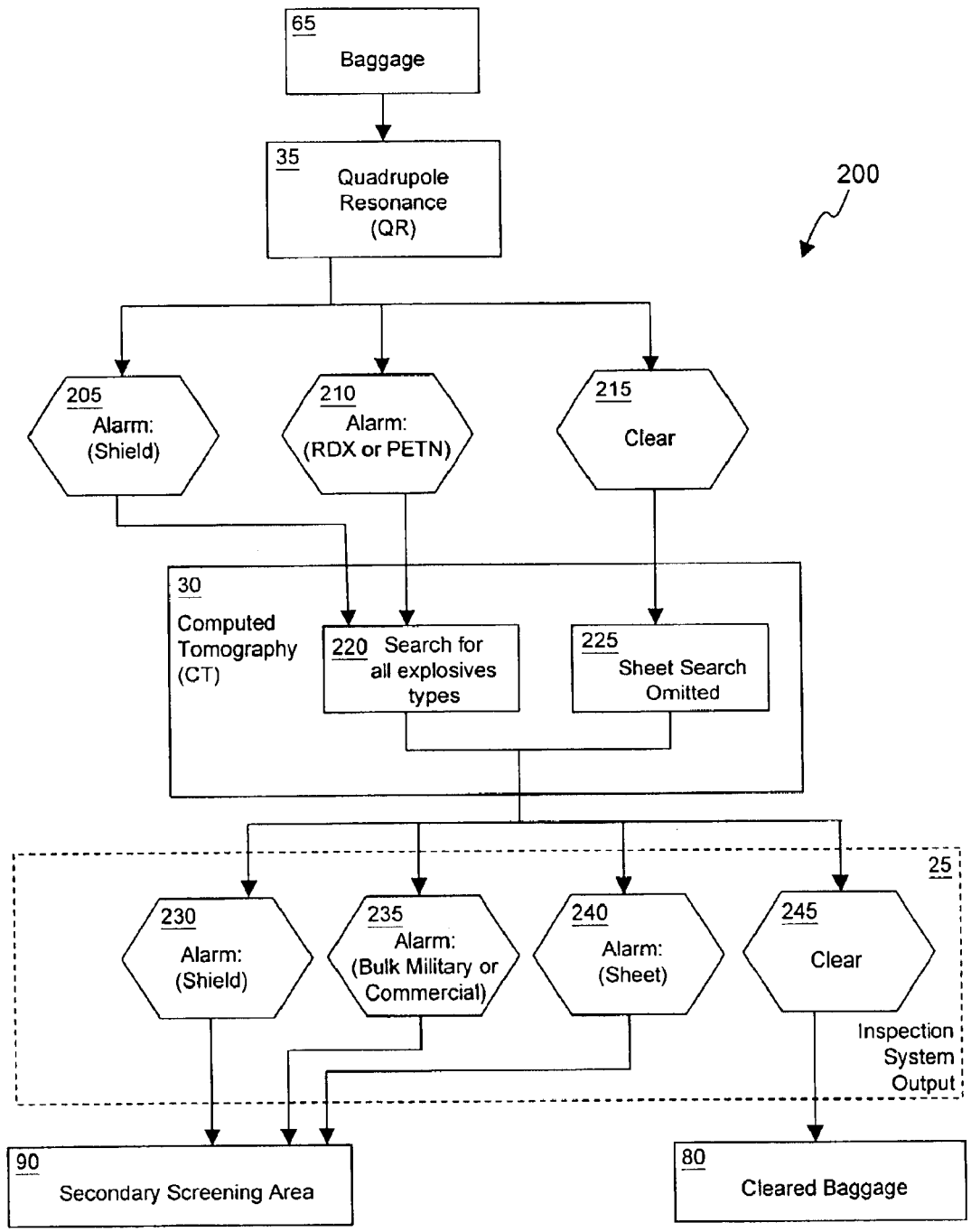
FIG. 5 is a block diagram showing a scanning protocol for implementing a baggage inspection system according to an alternative embodiment of the present invention.

FIG. 5 is a block diagram showing a scanning protocol for implementing a baggage inspection system according to an alternative embodiment of the present invention and will be described with reference to scanning system 10 shown in FIG. 1. This embodiment essentially reverses the order that the baggage is screened by the two sensor systems, while employing additional scanning logic within the CT sensor.

In this figure, baggage is shown initially being screened by the QR sensor to determine the presence or absence of RDX or PETN, and in some instances, the presence of shielding (blocks 65, 35). If the QR sensor detects shielding or alarms on RDX or PETN, the suspicious bag may be directed to the CT sensor where full explosives screening procedures may be performed (blocks 205, 210, 220). That is, if the QR sensor detects a threshold level of RDX or PETN, or is unable to appropriately interrogate the bag (shielding), the suspicious bag may then be fully screened by the CT sensor for military, commercial, and sheet explosives.

On the other hand, if the QR sensor indicates that the bag is free of RDX or PETN, the "partially cleared" baggage may undergo more limited explosives screening procedures at the CT sensor (blocks 215, 225). In particular, the CT sensor may screen the partially cleared bag for military and commercial explosives, and may therefore omit sheet explosives screening procedures. Omitting the sheet explosives search allows the CT sensor to screen baggage more quickly, thus increasing overall baggage throughput.

After scanning, the CT sensor may generate the appropriate shield or explosives alarms, resulting in the suspicious bag being directed to secondary screening area for further processing (blocks 230, 235, 240, 90). However, if no explosives or shielding are found, the baggage may be cleared by the system (blocks 245, 80).

In the embodiment depicted in FIG. 5, the CT sensor primarily operates in a reduced scanning mode (no sheet search), unless the QR sensor alarms on RDX or PETN. This reduced scanning mode facilitates overall inspection throughput while not significantly affecting rates of detection of sheet explosives since the sheet scan is performed by the QR sensor.

FIG. 6 is a truth table showing inspection logic for the scanning protocol depicted in FIG. 5. Once again, bulk military, commercial, and CT shield alarms are essentially determined by the CT sensor outputs. Sheet alarms, on the other hand, may be determined by performing a logical AND operation upon the sheet alarms of the CT and QR sensors. That is, the inspection system will only generate a sheet alarm if the CT sensor and the QR sensor both generate sheet alarms.

Figure 7:
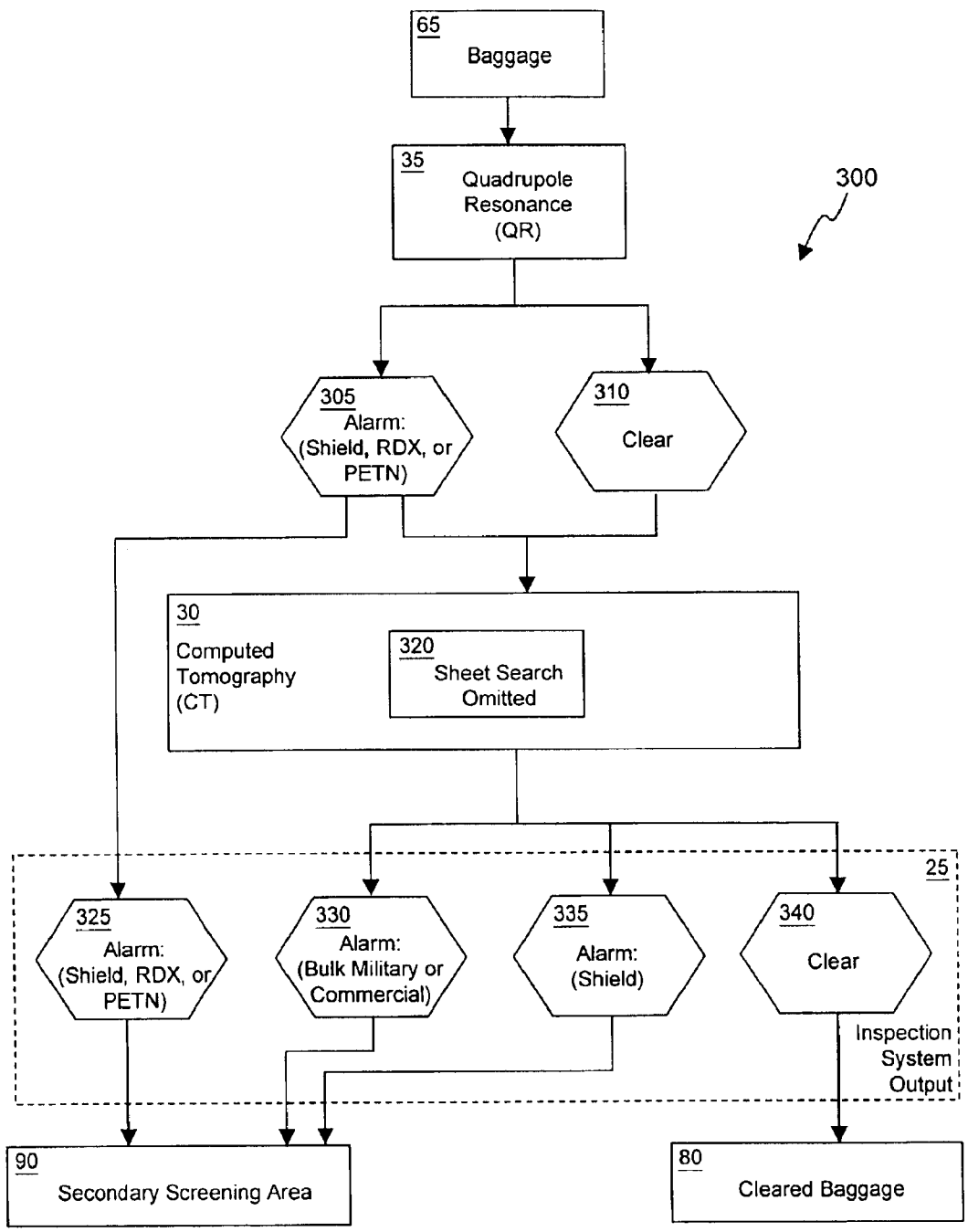
FIG. 7 is a flowchart showing a scanning protocol for implementing a baggage inspection system according to another alternative embodiment of the present invention.

FIG. 7 is a flowchart showing a scanning protocol for implementing a baggage inspection system according to another alternative embodiment of the present invention and will be described with reference to inspection system 10 shown in FIG. 1.

This embodiment is similar in many respects to the system described in FIG. 5. However, the inspection protocol depicted in FIG. 7 does not contain any conditional logic for baggage scanning at the CT sensor. All baggage is screened by the CT sensor operating in a reduced scanning mode (sheet search omitted). It also to be understood that no particular scanning order of the CT and QR sensors is required in this embodiment. Baggage may be screened first by the CT sensor, followed by screening by the QR sensor, or vice versa. Interchangeable scanning order is possible in this embodiment because conditional scanning logic is not employed here.

Referring still to FIG. 7, baggage may be initially screened by the QR sensor to determine the presence or absence of RDX, PETN, or shielding (blocks 65, 35, 305, 310). Regardless of the outcome of the scanning process, the baggage may then be directed to the CT sensor for further screening (block 30). In this embodiment, the CT sensor may screen the baggage for military and commercial explosives, while omitting sheet explosives screening procedures (block 320).

After scanning by both systems, the CT or QR sensor may generate the appropriate shield or explosives alarms, as depicted by blocks 325, 330, and 335, and the bag may be directed to secondary screening area 90 for additional processing. In the event that no explosives are detected by either system, the bag may be cleared by the system (blocks 340, 80).

FIG. 8 is a truth table showing inspection logic for the scanning protocol depicted in FIG. 7. Bulk military, commercial, and CT shield alarms are essentially determined by the CT sensor outputs. However, sheet alarms may be solely determined by output of the QR sensor since the CT sensor does not scan for sheet explosives in this embodiment.

Figure 9:
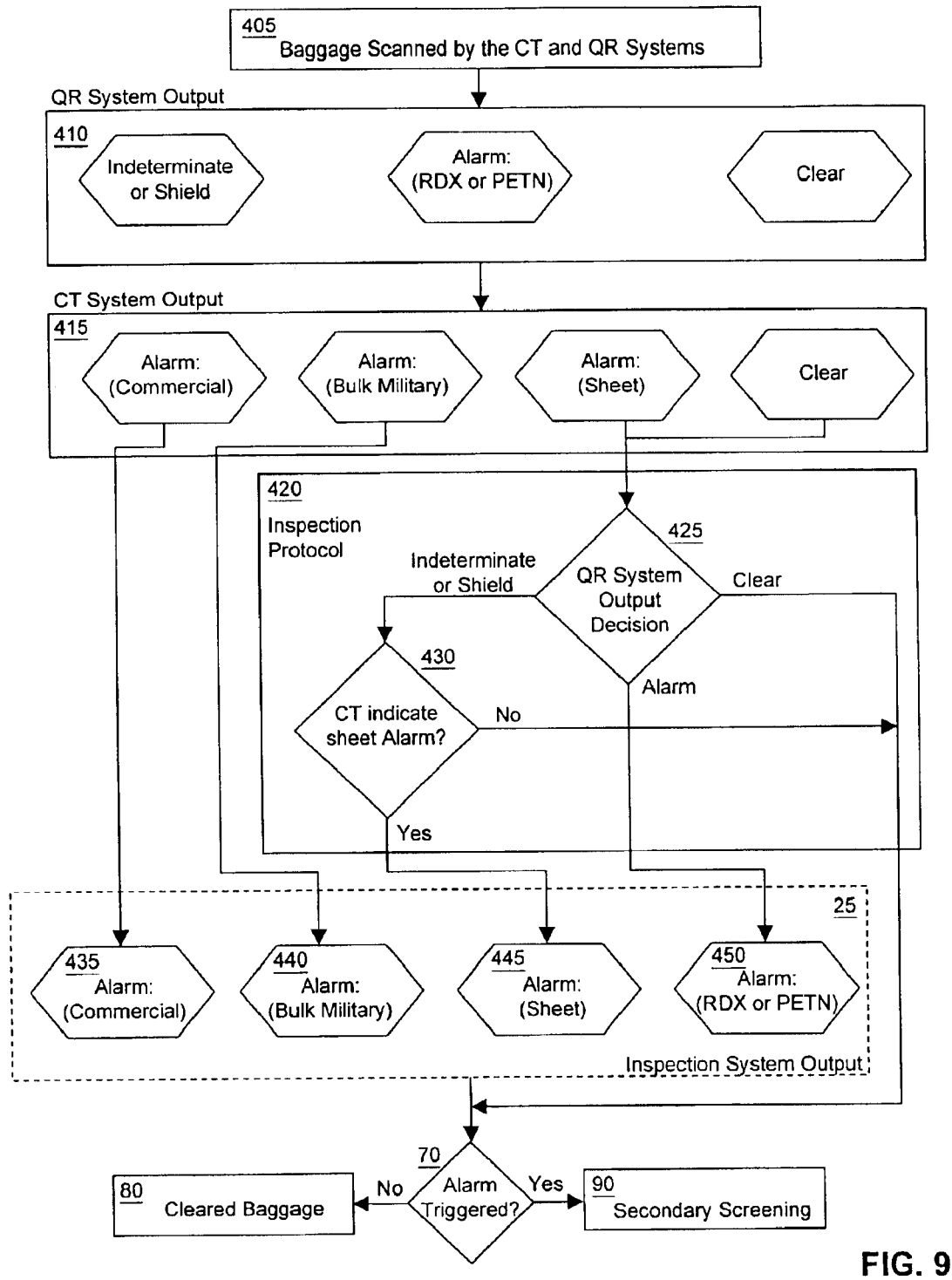
FIG. 9 is a flowchart showing a scanning protocol for implementing a baggage inspection system according to yet another alternative embodiment.

FIG. 9 is a flowchart showing a scanning protocol for implementing a baggage inspection system according to yet another alternative embodiment of the invention and will likewise be described with reference to inspection system 10 shown in FIG. 1.

In this embodiment, baggage does not have to be scanned by the CT and QR sensors in any particular order. Baggage may be first screened by the CT sensor followed by screening by the QR sensor, or vice versa (block 405).

As indicated in block 410, the QR sensor may provide three primary outputs; RDX/PETN alarm, indeterminate or shield, and clear. An RDX alarm indication, for example, means that the QR sensor has generated an RDX signal that exceeds an upper threshold value during baggage scanning. In contrast, a RDX clear indication means that the QR sensor has generated an RDX signal that falls below a lower threshold value during baggage scanning. Importantly, the upper and lower threshold values of the RDX signals are not the same, thus defining a mid-range of RDX signal values. This mid-range of RDX values will be referred to herein as a RDX indeterminate range.

One purpose for using the RDX indeterminate range is to denote RDX signals that are not clearly identifiable as an alarm (upper threshold) or free from explosives (lower threshold values). The just-described three-state logic for RDX also applies to PETN, such that the QR sensor may generate alarm, indeterminate, or clear indications for both RDX and PETN. The specifics of a three-state, RDX/PETN alarm threshold will be described in more detail with reference to the graph depicted in FIG. 11.

Referring still to FIG. 9, the output of the CT sensor may include one or more alarms, or a clear indication (block 415). For example, if the CT sensor detects commercial or bulk military explosives, the system may generate the appropriate commercial or bulk military alarms (blocks 435, 440). However, if the CT sensor detects sheet explosives, or determines that the baggage is free of explosives, then this data may be fed into inspection protocol block 420.

As indicated in decision block 425, the QR sensor output decision may first be examined. A QR clear indication will be generated if the QR sensor generates a RDX or PETN signal that falls below the predetermined lower RDX and PETN signal threshold, or no such signal at all. If the bag is cleared by the QR sensor, then control may flow to decision block 70 where the presence or absence of inspection system alarms may be determined. Note that a clear indication by the QR sensor can override a sheet alarm by the CT sensor.

Referring still to decision block 425, another scenario may be where the QR sensor has alarmed on RDX or PETN, which may be indicated by the QR sensor generating an RDX or PETN signal that exceeds a predetermined upper signal threshold. Thus, if the QR sensor alarms on RDX or PETN, then the inspection system output will generate the appropriate RDX/PETN alarm (block 450). In this scenario, the QR sensor may confirm a sheet alarm generated by the CT sensor, or may override a clear indication by the CT sensor.

A third possible scenario of decision block 425 is where the QR sensor has detected shielding or where the QR system has generated an indeterminate indication. In this situation, control may flow to decision block 430 where the CT sensor output is considered. For example, if the CT sensor did not generate a sheet alarm, then control may flow to decision block 70. In this situation, the lack of a CT sensor sheet alarm reconciles an indeterminate indication or shield alarm by the QR sensor.

On the other hand, if the CT sensor had generated a sheet alarm during baggage scanning, then the inspection system may generate the appropriate sheet alarm (block 445). In this scenario, a CT sensor sheet alarm overrides an indeterminate indication or shield alarm by the QR sensor. If desired, the inspection system output may display a combination of CT sheet alarms (block 445) and RDX or PETN alarms (block 450) in situations where the CT sensor alarms on sheet explosives and the QR sensor alarms on RDX or PETN.

As indicated in decision block 70, if inspection system output 25 indicates one or more alarms, then the suspicious bag may be identified as requiring alarm resolution and submitted to secondary screening (block 90). Otherwise, the bag may be directed to the cleared baggage area (blocks 80).

Although the order in which baggage is scanned by the CT and QR is not essential or critical to many embodiments of the invention, some implementations may benefit by scanning baggage with the QR sensor before the CT sensor. One reason for such an arrangement is to enhance the efficiency of the secondary baggage scanning process. For example, in situations where the inspection system generates an alarm based upon scanning data generated by the CT and QR sensors, the suspicious baggage may be directed to a secondary screening area, as previously described. In some instances, secondary screening may be performed using CT sensor 30. If the CT sensor is arranged after the QR sensor, then any suspicious baggage requiring more extensive interrogation will not have to be reintroduced to the CT sensor since it will already be located within or nearby this sensor.

Although the present invention may be implemented using the exemplary series of operations shown in the various flowcharts presented herein, those of ordinary skill in the art will realize that additional or fewer operations may be performed. Moreover, it is to be understood that the order of operations shown in these flowcharts is merely exemplary and that in many cases, no specific order of operation is required.

FIG. 10 is a truth table showing inspection logic that may be used for implementing the three-state scanning protocol depicted in FIG. 9. If the CT sensor alarmed on bulk military, then regardless of the QR scanning results, the inspection system will output a bulk military alarm. However, a QR sensor alarm on this type of explosive will override a clear indication by the CT sensor. With regard to sheet explosives, the QR sensor may either clear a CT sensor alarm, or override a CT sensor clear indication. Commercial and CT shield alarms are handled in a fashion similar to other embodiments.

Figure 11:
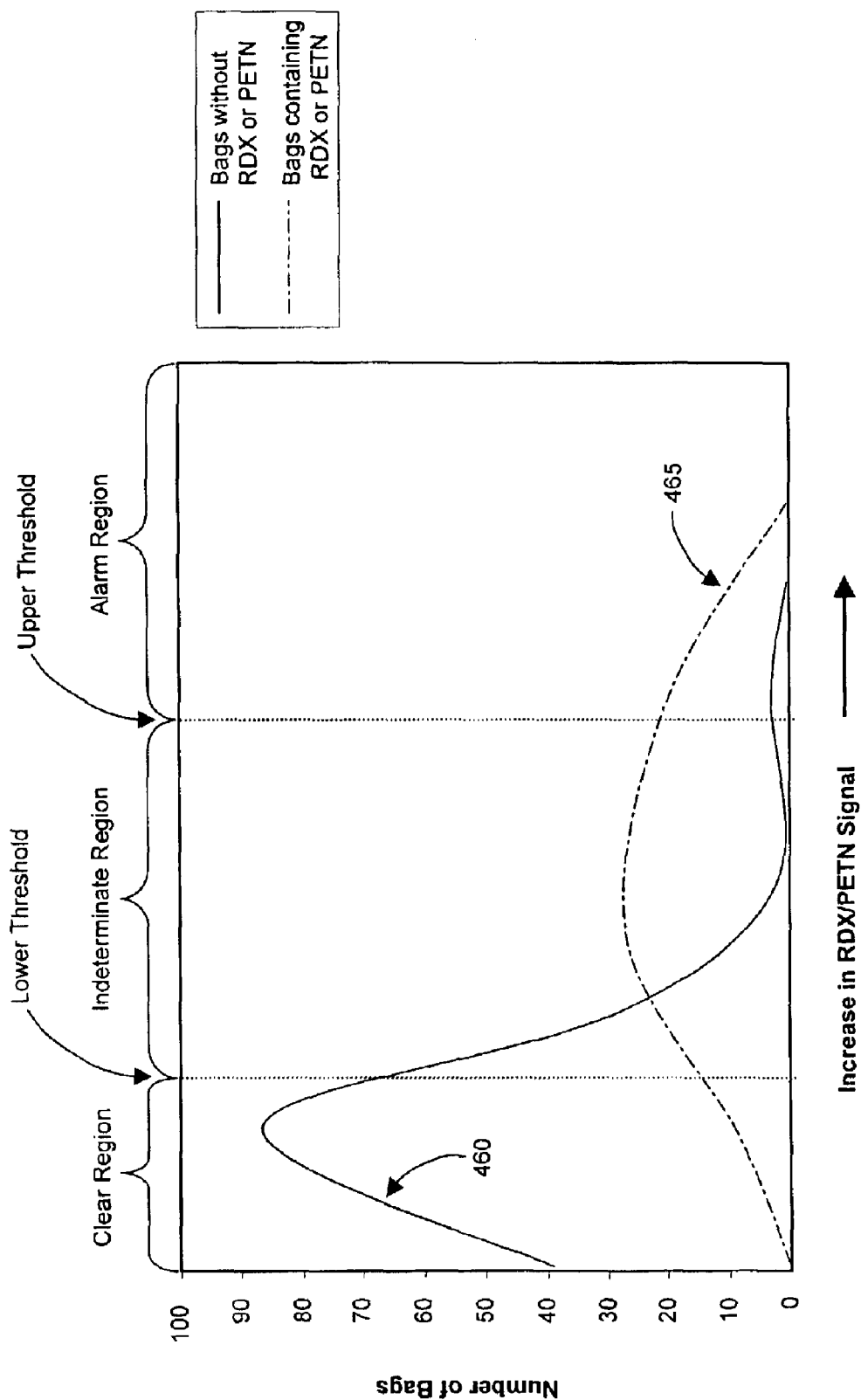
FIG. 11 is a graph showing a distribution of bags in relationship to a RDX or PETN signal generated by a QR sensor during a typical scanning process.

FIG. 11 is a graph showing a distribution of bags in relationship to a RDX or PETN signal generated by a QR sensor during a scanning process, and will again be described with reference to inspection system 10 shown in FIG. 1, and the inspection protocol of FIG. 9.

The X-axis of this graph represents a RDX or PETN signal that increases in magnitude along this axis. The Y-axis represents the number of bags that generated a particular RDX or PETN signal. The RDX and PETN signal parameters may be obtained from the magnitude of the emitted QR signals at the resonance frequency and thus, the RDX signals will vary from PETN signals. For convenience, further description of this graph will be made with reference to RDX signals, but it is to be understood that these principles apply equally to PETN signals, as well as signals generated from compounds containing both RDX and PETN (for example, Semtex H).

The graph is shown divided into three separate regions defined by lower and upper RDX signal thresholds. In particular, a lower threshold defines the transition from a clear region to the indeterminate region, while the upper threshold defines the transition from the indeterminate region to the alarm region. The solid curve 460 represents the number of bags that are free of compounds containing RDX, and the dashed curve 465 represents the number of bags containing materials having RDX. In general, as the RDX signal increases in magnitude, the number of bags free of RDX decreases, while the number of threat-carrying bags contain RDX increases. However, as shown in the area defined by the indeterminate region, this general rule is not absolute. For instance, the indeterminate region has a sizeable number of threat-carrying (curve 465) and non-threat-carrying, innocent bags (curve 460).

The significance of the alarm region is that while a number of bags that actually contain RDX fall within this region, there are a relatively few number of bags that are free of RDX. Setting the upper threshold at this location raises the confidence that the bag triggering5 the alarm contains RDX, while providing a relatively low false alarm rate.

Modifying the upper threshold value can affect the possibility of detection, but may also increase the false alarm rate. For example, as the upper threshold value is reduced (moved to left in the graph), the number of bags containing RDX increases. However, this modification would also result in an increased number of alarms generated by bags free from RDX. As such, reducing the upper threshold RDX signal value may increase the possibility of detection, but at the cost of an increase in false alarm rates. Accordingly, the upper threshold value may be tuned to achieve a particular level of additional sheet detection while maintaining a desired false alarm rate. In some embodiments, a suitable RDX upper threshold value may be where the false alarm rate of 0.4–1.0%, or lower, can be realized.

The clear region of the graph defines an area that contains a significant number of bags that are free from RDX, as well as a small number of bags that actually contain RDX. The lower threshold value has the function of discarding false alarms from the CT sensor. For example, as previously described, only bags that alarm for sheet explosives in the CT sensor will be subjected to the lower threshold test. The lower threshold value is typically selected with care so that the QR sensor does not clear an excessive number of bags that contain actual threats. An appropriate lower threshold value may be, for example, where 5–10% of the bags that the CT sensor correctly alarmed on sheet explosives containing RDX will be cleared.

Particular examples of suitable upper and lower threshold values have been described. However, it is to be understood that these particular values have been provided as examples only, and that the present invention does not require any particular upper and lower threshold values. Accordingly, the performance of the inspection system may be optimized to achieve a desired or required explosives detection rate or false alarm rate by tuning the lower or upper threshold values, or both.

Many embodiments have been described using the signal amplitude of RDX and PETN QR signals to trigger an alarm. However, other signal parameters may be used to supplement or replace these signals if so desired. Consider, for example, the situation where the scanned bag contains materials preventing or inhibiting QR interrogation. In this scenario, the QR sensor may generate an unusually high QR signal, often referred to as "QR" ringing which includes, but is not limited to, magnetostrictive ringing. Generated QR ringing signals may be used alone, or in conjunction with the RDX and PETN signals to trigger a QR alarm.

Figure 12:
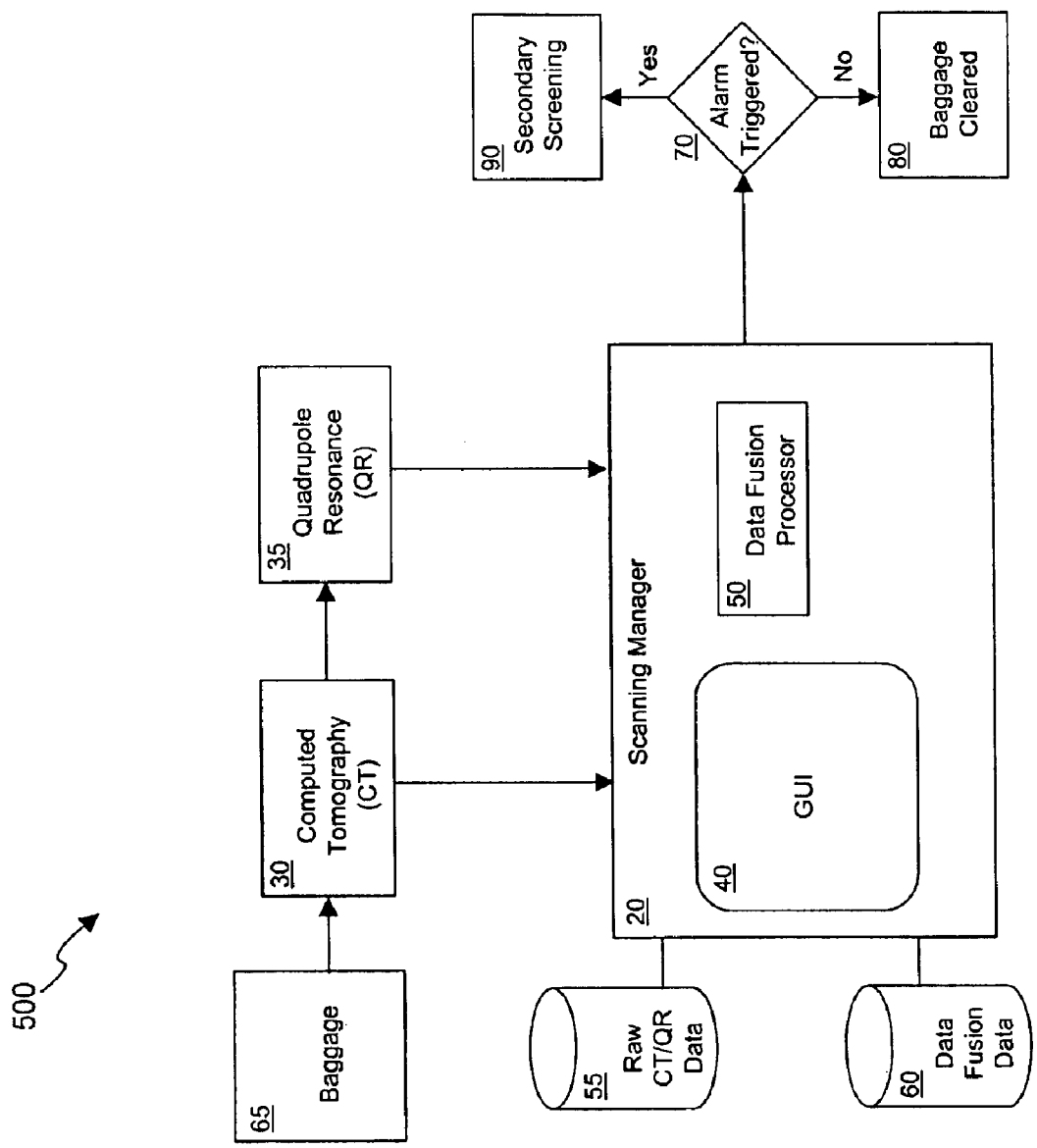
FIG. 12 is a block diagram of an alternative embodiment of a baggage inspection system of the present invention.

Referring now to FIG. 12, a block diagram of an alternative embodiment of a baggage inspection system 500 of the present invention is shown. Similar to the inspection system shown in FIG. 1, system 500 generally includes scanning manager 20 configured with CT sensor 30 and QR sensor 35. The inspection system output unit has been omitted for clarity.

A notable distinction between these inspection systems relates to the physical arrangement of the CT and QR sensors. In particular, the CT and QR sensors shown in FIG. 12 are implemented as standalone systems, in contrast to the integrated design shown in FIG. 1.

In the FIG. 12 embodiment, baggage scanning may proceed as follows. First, baggage may be sequentially scanned by the CT and QR sensors using any of the methods and techniques described herein. Transporting the baggage between the standalone CT and QR system may be accomplished using known baggage handling methods such as a baggage conveyor and baggage tracking system. A baggage tracking system is often utilized so that the data generated during scanning at the CT and QR sensors may be properly associated with each individual bag.

After scanning, the CT and QR sensor may communicate the necessary scanning data to QRCT manager 20 so that the data may be analyzed to generate an alarm or clear indication. As indicated in block 70, if an alarm is generated, then the suspicious baggage may be directed to secondary screening area 90; otherwise, the baggage may be directed to the cleared baggage area 80.

The CT and QR sensors may be implemented as standalone systems placed in close physical proximity or physically separated. Almost any configuration may be realized as long as baggage can be directed through each of these systems, and the generated scanning data is communicated to the QRCT manager for processing.

Figure 13:
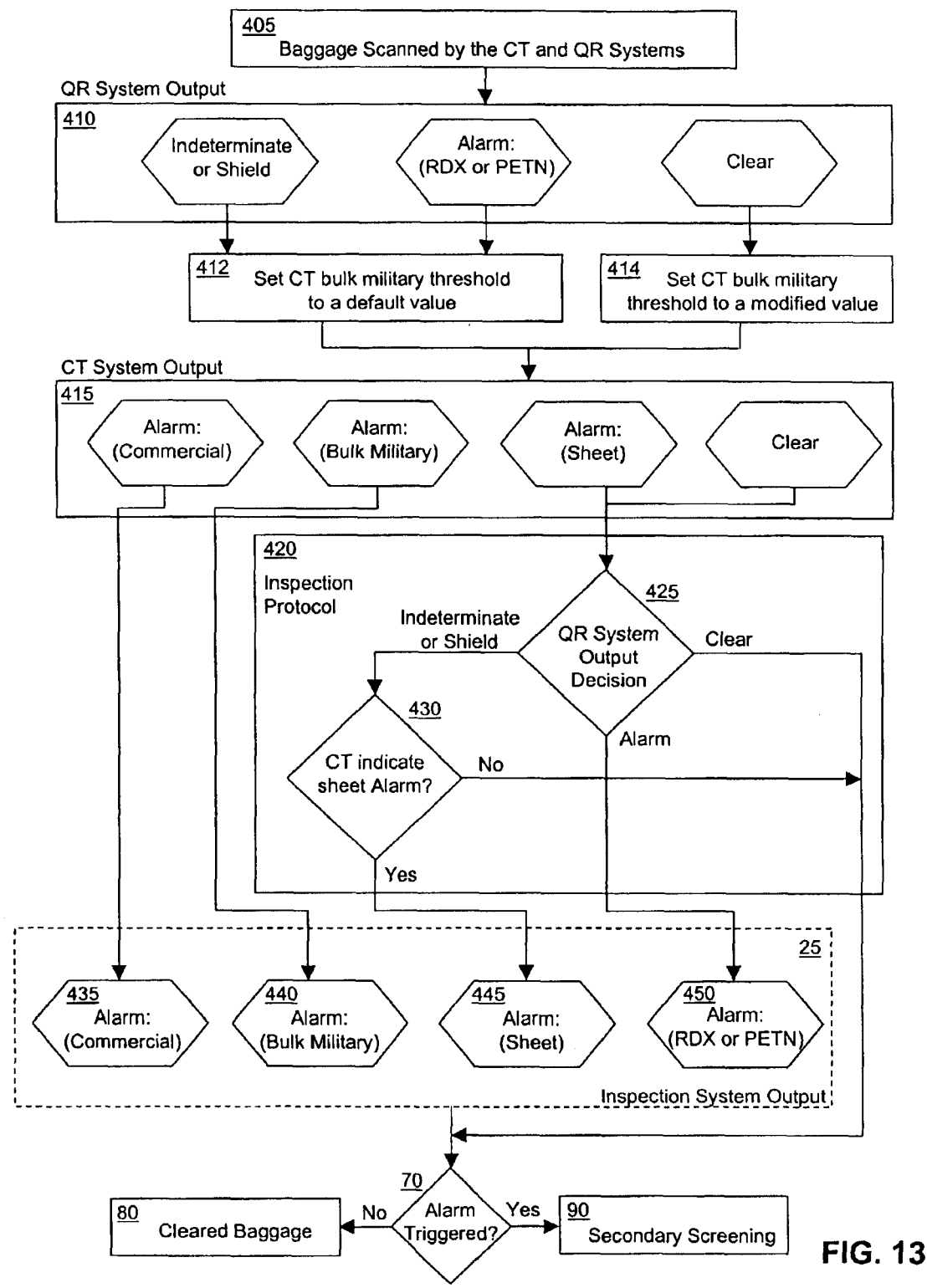
FIG. 13 is a flowchart showing a scanning protocol for implementing a baggage inspection system according to an alternative embodiment of the invention.

FIG. 13 is a flowchart showing a scanning protocol for implementing a baggage inspection system according to another alternative embodiment of the invention and will likewise be described with reference to inspection system 10 shown in FIG. 1. This embodiment is similar in many respects to the system depicted in FIG. 9. However, the inspection protocol depicted in FIG. 13 implements additional inspection logic for detecting different classes of explosives within the bulk military category. For reasons that will become clear, this embodiment provides for the clearing of additional bulk military alarms, without reducing explosive detection rates.

In many embodiments, the CT sensor is configured to detect all types of explosives within the bulk military class. Recall that the bulk military explosives classification may be generally defined to include plastic (explosive materials that contain RDX and/or PETN) and non-plastic (for example, TNT) types of explosives. Since the CT sensor typically uses, among other parameters, a mass threshold in determining whether or not to alarm, this mass threshold is set to a level where all desired types of explosives can be detected. To ensure proper detection of dangerous amounts of plastic and non-plastic types of explosives within the bulk military class, the CT sensor should therefore be set to a default threshold to detect desired amounts of each of these types of explosives. Accordingly, if the possibility of plastic explosives can be confidently eliminated, then the explosives detection threshold for the bulk military explosives scanning process may be modified to only detect desired amounts of non-plastic types of explosives.

An example of a baggage scanning process where the bulk military explosives scanning performed by the CT sensor utilizes a variable explosives detection threshold will now be described. Referring still to FIG. 13, in a manner similar to other embodiments, baggage may be scanned by the CT and QR sensors in any desired order (block 405). After scanning, the QR sensor may provide three primary outputs; RDX/PETN alarm, indeterminate or shield, and clear (block 410).

Next, the output of the QR sensor system is considered. If the QR system detects RDX or PETN, shielding, or provides an indeterminate indication, then the CT bulk military explosives detection threshold may be set to a default value that permits the detection of a predetermined or desired threat quantity of plastic, as well as non-plastic types of explosives within the bulk military class (block 412).

On the other hand, if the QR system determines that the bag is clear of RDX and PETN, the resulting clear indication permits the CT bulk military explosives detection threshold to be set to a modified value that eliminates plastic explosives detection, while still permitting the detection of non-plastic types of explosives within the bulk military class. This protocol may be implemented without sacrificing detection rates since the QR sensor has confidently eliminated the possibility that plastic explosives are contained within the bag.

The inspection protocol may proceed as follows. As indicated in block 415, the CT sensor determines the presence or absence of bulk military explosives based upon the CT bulk military explosives detection threshold value (default or modified) determined in blocks 412 or 414.

In one scenario, where the QR sensor generated an alarm or provided an indeterminate indication, the CT sensor would generate bulk military alarms based upon the default CT bulk military explosives detection threshold to ensure that plastic and non-plastic types of explosives within the bulk military class are identified. In another scenario, where the QR sensor determined that the bag was free of RDX and PETN (QR clear indication), then the CT sensor would generate bulk military alarms based upon a modified CT bulk military explosives detection threshold. In this second scenario, the CT sensor will not alarm on bulk military explosives (plastic or non-plastic) falling below the modified CT bulk military explosives detection threshold.

Regardless of the CT bulk military explosives detection threshold setting, if the CT sensor detects sufficient amounts of commercial or bulk military explosives, the system may generate the appropriate commercial or bulk military alarms (blocks 435, 440). However, if the CT sensor detects sheet explosives, or determines that the baggage is free of explosives, then this data may be fed into inspection protocol block 420. Further scanning may be accomplished in a fashion similar to that depicted in FIG. 9.

It is to be realized that the present invention does not require any particular CT bulk military explosives detection threshold values, and any practical threshold values that provide a desired combination of false alarm rate and possibility of detection of the desired type of explosives (plastic and non-plastic) may be implemented.

While the invention has been described in detail with reference to disclosed embodiments, various modifications within the scope of the invention will be apparent to those of ordinary skill in this technological field. It is to be appreciated that features described with respect to one embodiment typically may be applied to other embodiments. Therefore, the invention properly is to be construed with reference to the claims.

What is claimed is:

1. A method for detecting explosives in baggage, said method comprising:

X-ray scanning said baggage for explosives using a X-ray sensor adapted to automatically, selectively generate alarm and clear signals to respectively identify the presence or absence of said explosives; and processing said signals generated by said X-ray sensor, wherein if said X-ray sensor generates an alarm signal for sheet explosives resulting from said X-ray scanning, then said method further comprises:

quadrupole resonance (QR) scanning said baggage using a QR sensor, wherein said QR sensor is adapted to generate QR signals in response to explosive compounds containing QR responsive materials; and wherein if said QR sensor generates a QR signal that meets or exceeds a predetermined threshold, then a QR system alarm is triggered and said baggage is identified as requiring alarm resolution.

2. The method according to claim 1, wherein:

if said X-ray sensor generates an alarm signal for bulk military or commercial explosives resulting from said X-ray scanning, then a bulk military or commercial system alarm is triggered and said baggage is identified as requiring said alarm resolution, and wherein;

if said QR sensor generates a QR signal that falls below said predetermined threshold, then a baggage clear indication is triggered that overrides any alarm signal for sheet explosives generated by said X-ray sensor.

3. The method according to claim 1, wherein if said X-ray sensor generates a clear signal indicating that said baggage is free from said explosives, then said baggage is identified as not requiring further scanning.

4. The method according to claim 1, wherein said X-ray sensor comprises an X-ray computed tomography (CT) sensor.

5. The method according to claim 1, wherein said X-ray sensor comprises a single-view X-ray sensor.

6. The method according to claim 1, wherein said X-ray sensor comprises a multi-view X-ray sensor.

7. The method according to claim 1, wherein said QR and X-ray sensors are integrated into a single baggage inspection system.

8. The method according to claim 1, wherein said QR and X-ray sensors are configured as standalone sensor units.

9. The method according to claim 1, wherein said QR and X-ray sensors are further adapted with sensors to automatically generate alarm signals to respectively identify QR or X-ray shielding present in said baggage.

10. The method according to claim 1, wherein said QR signals comprise RDX and PETN signals responsive to explosive compounds respectively containing RDX or PETN.

11. A system for detecting explosives in baggage, said system comprising:

an X-ray sensor adapted to automatically, selectively generate alarm and clear signals to respectively identify the presence or absence of explosives during X-ray scanning of said baggage;

a quadrupole resonance (QR) sensor adapted to generate QR signals in response to explosive compounds containing QR responsive materials; and a processor for processing said signals generated by said QR and X-ray sensors, and wherein:

if said X-ray sensor generates an alarm signal for sheet explosives resulting from said X-ray scanning, then said baggage is QR scanned by said QR sensor, and wherein;

if said QR sensor generates a QR signal that meets or exceeds a predetermined threshold, then a QR system alarm is triggered and said baggage is identified as requiring alarm resolution.

12. The system according to claim 11, wherein:

if said X-ray sensor generates an alarm signal for said bulk military or commercial explosives resulting from said X-ray scanning, then a bulk military or commercial system alarm is triggered and said baggage is identified as requiring said alarm resolution, and wherein;

if said QR sensor generates a QR signal that falls below said predetermined threshold, then a baggage clear indication is triggered that overrides any alarm signal for sheet explosives generated by said X-ray sensor.

13. The system according to claim 11, wherein if said X-ray sensor generates a clear signal indicating that said baggage is free from said sheet explosives, then said baggage is identified as not requiring further scanning.

14. The system according to claim 11, wherein said X-ray sensor comprises an X-ray computed tomography (CT) sensor.

15. The system according to claim 11, wherein said X-ray sensor comprises a single-view X-ray sensor.

16. The system according to claim 11, wherein said X-ray sensor comprises a multi-view X-ray sensor.

17. The system according to claim 11, wherein said QR and X-ray sensors are integrated into a single baggage inspection system.

18. The system according to claim 11, wherein said QR and X-ray sensors are configured as standalone sensor units.

19. The system according to claim 11, wherein said QR and X-ray sensors are further adapted with sensors to automatically generate alarm signals to respectively identify QR or X-ray shielding present in said baggage.

20. The system according to claim 11, wherein said QR signals comprise RDX and PETN signals responsive to explosive compounds respectively containing RDX or PETN.

21. A method for detecting explosives in baggage, said method comprising:

quadrupole resonance (QR) scanning said baggage using a QR sensor adapted to generate QR signals in response to explosive compounds containing QR responsive materials;

X-ray scanning said baggage for non-sheet configurations of explosives using a X-ray sensor, wherein said X-ray sensor is adapted to automatically, selectively generate alarm and clear signals to respectively identify the presence or absence of said non-sheet configurations of explosives, and wherein:

if said QR sensor generates a QR signal resulting from said QR scanning that meets or exceeds a predetermined threshold, then said method further comprises X-ray scanning said baggage for sheet explosives to automatically, selectively generate alarm and clear signals to respectively identify the presence or absence of said sheet explosives; and processing said signals generated by said X-ray and QR sensors, wherein if said X-ray sensor generates an alarm signal for said non-sheet or sheet explosives resulting from said X-ray scanning, then a system alarm is triggered and said baggage is identified as requiring said alarm resolution.

22. The method according to claim 21, wherein if said X-ray sensor generates a clear signal indicating that said baggage is free from said non-sheet or sheet explosives, then said baggage is identified as being free from explosives.

23. The method according to claim 21, wherein said X-ray sensor comprises an X-ray computed tomography (CT) sensor.

24. The method according to claim 21, wherein said X-ray sensor comprises a single-view X-ray sensor.

25. The method according to claim 21, wherein said X-ray sensor comprises a multi-view X-ray sensor.

26. The method according to claim 21, wherein said QR and X-ray sensors are integrated into a single baggage inspection system.

27. The method according to claim 21, wherein said QR and X-ray sensors are configured as standalone sensor units.

28. The method according to claim 21, wherein said QR and X-ray sensors are further adapted with sensor to automatically generate alarm signals to respectively identify QR and X-ray shielding present in said baggage.

29. The method according to claim 21, wherein said QR signals comprise RDX and PETN signals responsive to explosive compounds respectively containing RDX or PETN.

30. A system for detecting explosives in baggage, said system comprising:

a quadrupole resonance (QR) sensor adapted to generate QR signals in response to explosive compounds containing QR responsive materials, wherein said QR signals are obtained during QR scanning of said baggage;

an X-ray sensor adapted to automatically, selectively generate alarm and clear signals to respectively identify the presence or absence of explosives; and a processor for processing said signals generated by said QR and X-ray sensors, and wherein:

if said QR sensor generates a QR signal that meets or exceeds a predetermined threshold, then said baggage is X-ray scanned by said X-ray sensor for sheet and non-sheet types of said explosives to automatically, selectively generate alarm and clear signals to respectively identify the presence or absence of said sheet and non-sheet types of explosives, otherwise, if said QR sensor generates a QR signal that falls below said predetermined threshold, then said baggage is X-ray scanned by said X-ray sensor for non-sheet types of said explosives to automatically, selectively generate an alarm or clear signals to respectively identify the presence or absence of said non-sheet types of explosives.

31. The system according to claim 30, wherein if said X-ray sensor generates a clear signal for indicating that said baggage is free from said sheet and non-sheet types of explosives, then said baggage is identified as not requiring further scanning.

32. The system according to claim 30, wherein if said X-ray sensor generates an alarm signal for said sheet or non-sheet types of explosives resulting from said X-ray scanning, then a system alarm is triggered and said baggage is identified as requiring alarm resolution.

33. The system according to claim 30, wherein said X-ray sensor comprises an X-ray computed tomography (CT) sensor.

34. The system according to claim 30, wherein said X-ray sensor comprises a single-view X-ray sensor.

35. The system according to claim 30, wherein said X-ray sensor comprises a multi-view X-ray sensor.

36. The system according to claim 30, wherein said QR and X-ray sensors are integrated into a single baggage inspection system.

37. The system according to claim 30, wherein said QR and X-ray sensors are configured as standalone sensor units.

38. The system according to claim 30, wherein said QR and X-ray sensors are further adapted sensors to automatically generate alarm signals to respectfully identify QR or X-ray shielding present in said baggage.

39. The system according to claim 30, wherein said QR signals comprise RDX and PETN signals responsive to explosive compounds respectively containing RDX or PETN.

40. A method for detecting explosives in baggage, said method comprising:

quadrupole resonance (QR) scanning said baggage using a QR sensor adapted to generate QR signals in response to explosive compounds containing QR responsive materials;

X-ray scanning said baggage for non-sheet types of explosives using a X-ray sensor adapted to automatically, selectively generate alarm and clear signals to respectively identify the presence or absence of said non-sheet types of explosives; and processing said signals generated by said X-ray and QR sensors, wherein:

if said QR sensor generates a QR signal that meets or exceeds a predetermined threshold, then a QR system alarm is triggered and said baggage is identified as requiring alarm resolution; and wherein if said X-ray sensor generates an alarm signal for said non-sheet types of explosives resulting from said X-ray scanning, then a system alarm is triggered and said baggage is identified as requiring said alarm resolution.

41. The method according to claim 40, wherein:

if said X-ray sensor generates a clear signal indicating that said baggage is free from said non-sheet types of explosives, then said baggage is identified as not requiring said alarm resolution, subject to any alarms generated by said QR sensor, and wherein;

if said QR sensor generates a QR signal that falls below said predetermined threshold, then a baggage clear indication is triggered and said baggage is identified as not requiring said alarm resolution, subject to any alarms generated by said X-ray sensor.

42. The method according to claim 40, wherein said X-ray sensor comprises an X-ray computed tomography (CT) sensor.

43. The method according to claim 40, wherein said X-ray sensor comprises a single-view X-ray sensor.

44. The method according to claim 40, wherein said X-ray sensor comprises a multi-view X-ray sensor.

45. The method according to claim 40, wherein said QR and X-ray sensors are integrated into a single baggage inspection system.

46. The method according to claim 40, wherein said QR and X-ray sensors are configured as standalone sensor units.

47. The method according to claim 40, wherein said QR and X-ray sensors are further adapted to automatically generate alarm signals to identify shielding present in said baggage.

48. The method according to claim 40, wherein said QR scanning is performed prior to said X-ray scanning.

49. The method according to claim 40, wherein said QR scanning is performed after said X-ray scanning.

50. The method according to claim 40, wherein said QR signals comprise RDX and PETN signals responsive to explosive compounds respectively containing RDX or PETN.

51. A system for detecting explosives in baggage, said system comprising:
   a quadrupole resonance (QR) sensor adapted to generate QR signals in response to explosive compounds containing QR responsive materials, wherein said QR signals are obtained during QR scanning of said baggage;
   an X-ray sensor adapted to automatically, selectively generate alarm and clear signals to respectively identify the presence or absence of non-sheet types of explosives during X-ray scanning of said baggage; and
   a processor for processing said signals generated by said QR and X-ray sensors, and wherein:
      if said X-ray sensor generates an alarm signal for said non-sheet explosives resulting from said X-ray scanning, then a system alarm is triggered and said baggage is identified as requiring alarm resolution, and wherein;
      if said QR sensor generates a QR signal that meets or exceeds a predetermined threshold, then a QR system alarm is triggered and said baggage is identified as requiring said alarm resolution.

52. The system according to claim 51, wherein: if said X-ray sensor generates a clear signal indicating that said baggage is free from said non-sheet types of explosives, then said baggage is identified as not requiring said alarm resolution, subject to any alarms generated by said QR sensor, and wherein;
   if said QR sensor generates a QR signal that falls below said predetermined threshold, then a baggage clear indication is triggered and said baggage is identified as not requiring said alarm resolution, subject to any alarms generated by said X-ray sensor.

53. The system according to claim 51, wherein said X-ray sensor comprises an X-ray computed tomography (CT) sensor.

54. The system according to claim 51, wherein said X-ray sensor comprises a single-view X-ray sensor.

55. The system according to claim 51, wherein said X-ray sensor comprises a multi-view X-ray sensor.

56. The system according to claim 51, wherein said QR and X-ray sensors are integrated into a single baggage inspection system.

57. The system according to claim 51, wherein said QR and X-ray sensors are configured as standalone sensor units.

58. The system according to claim 51, wherein said QR and X-ray sensors are further adapted with sensors to automatically generate alarm signals to respectively identify QR and X-ray shielding present in said baggage.

59. The system according to claim 51, wherein said QR scanning is performed prior to said X-ray scanning.

60. The system according to claim 51, wherein said QR scanning is performed after said X-ray scanning.

61. The system according to claim 51, wherein said QR signals comprise RDX and PETN signals responsive to explosive compounds respectively containing RDX or PETN.

62. A method for detecting explosives in baggage, said method comprising:
   quadrupole resonance (QR) scanning said baggage using a QR sensor adapted to generate QR signals in response to explosive compounds containing QR responsive materials;
   X-ray scanning said baggage for explosives using a X-ray sensor adapted to automatically, selectively generate alarm and clear signals to respectively identify the presence or absence of said explosives; and
   processing said signals generated by said X-ray and QR sensors, wherein:
      if said QR sensor generates a QR signal that meets or exceeds a predetermined upper threshold, then a QR system alarm is triggered and said baggage is identified as requiring alarm resolution, even if said X-ray sensor generates a clear signal for sheet explosives resulting from said X-ray scanning; and wherein
      if said QR sensor generates a QR signal that falls below a lower predetermined threshold, then a QR clear indication is triggered, even if said X-ray sensor generates an alarm for sheet explosives resulting from said X-ray scanning; and wherein
      if said QR sensor generates a QR signal that falls between said predetermined upper and lower thresholds, then an indeterminate indication is triggered, said method further comprises:
         if said X-ray sensor generates a clear signal for sheet explosives resulting from said X-ray scanning, then said baggage is identified as not requiring said alarm resolution, subject to any other alarms generated by said X-ray sensor, otherwise,
         if said X-ray sensor generates an alarm signal for sheet explosives resulting from said X-ray scanning, then a sheet system alarm is triggered and said baggage is identified as requiring said alarm resolution.

63. The method according to claim 62, wherein if said X-ray sensor generates an alarm signal for non-sheet types of explosives resulting from said X-ray scanning, then a non-sheet system alarm is triggered and said baggage is identified as requiring said alarm resolution.

64. The method according to claim 62, wherein said X-ray sensor comprises an X-ray computed tomography (CT) sensor.

65. The method according to claim 62, wherein said X-ray sensor comprises a single-view X-ray sensor.

66. The method according to claim 62, wherein said X-ray sensor comprises a multi-view X-ray sensor.

67. The method according to claim 62, wherein said QR and X-ray sensors are integrated into a single baggage inspection system.

68. The method according to claim 62, wherein said QR and X-ray sensors are configured as standalone sensor units.

69. The method according to claim 62, wherein said QR and X-ray sensors are further adapted with sensors to automatically generate alarm signals to respectively identify QR and X-ray shielding present in said baggage.

70. The method according to claim 62, wherein said QR scanning is performed prior to said X-ray scanning.

71. The method according to claim 62, wherein said QR scanning is performed after said X-ray scanning.

72. The method according to claim 62, wherein said QR signals comprise RDX and PETN signals responsive to explosive compounds respectively containing RDX or PETN.

73. The method according to claim 62, wherein;

if said quadrupole resonance (QR) sensor triggers said QR system alarm or said indeterminate indication, then said X-ray sensor is further adapted to automatically, selectively generate bulk military alarm and clear signals to respectively identify the presence or absence of a default threshold amount of a bulk military class of explosives, wherein said default threshold amount identifies predetermined threat quantities of plastic and non-plastic types of explosives within said bulk military class of explosives; and wherein if said QR sensor triggers said QR clear indication, then said X-ray sensor is further adapted to automatically, selectively generate bulk military alarm and clear signals to respectively identify the presence or absence of a modified threshold amount of said bulk military class of explosives, wherein said modified threshold amount only identifies predetermined threat quantities of non-plastic types of explosives within said bulk military class of explosives.

74. A system for detecting explosives in baggage, said system comprising:

a quadrupole resonance (QR) sensor adapted to generate QR signals in response to explosive compounds containing QR responsive materials, wherein said QR signals are obtained during QR scanning of said baggage;

an X-ray sensor adapted to automatically generate alarm and clear signals to respectively identify the presence or absence of explosives during X-ray screening of said baggage; and a processor for processing said signals generated by said QR and X-ray sensors, and wherein:

if said QR sensor generates a QR signal that meets or exceeds a predetermined upper threshold, then a QR system alarm is triggered and said baggage is identified as requiring alarm resolution, even if said X-ray sensor generates a clear signal for sheet explosives resulting from said X-ray scanning, and wherein;

if said QR sensor generates a QR signal that falls below a lower predetermined threshold, then a QR clear indication is triggered, even if said X-ray sensor generates an alarm for sheet explosives resulting from said X-ray scanning, and wherein;

if said QR sensor generates a QR signal that falls between said predetermined upper and lower thresholds, then an indeterminate indication is triggered, and wherein;

if said X-ray sensor generates a clear signal for sheet explosives resulting from said X-ray scanning, then said baggage is identified as not requiring said alarm resolution, subject to any other alarms generated by said X-ray sensor otherwise, if said X-ray sensor generates an alarm signal for sheet explosives resulting from said X-ray scanning, then a sheet system alarm is triggered and said baggage is identified as requiring said alarm resolution.

75. The system according to claim 74, wherein if said X-ray sensor generates an alarm signal for non-sheet types of explosives resulting from X-ray scanning, then a non-sheet system alarm is triggered and said baggage is identified as requiring said alarm resolution.

76. The system according to claim 74, wherein said X-ray sensor comprises an X-ray computed tomography (CT) sensor.

77. The system according to claim 74, wherein said X-ray sensor comprises a single-view X-ray sensor.

78. The system according to claim 74, wherein said X-ray sensor comprises a multi-view X-ray sensor.

79. The system according to claim 74, wherein said QR and X-ray sensors are integrated into a single baggage inspection system.

80. The system according to claim 74, wherein said QR and X-ray sensors are configured as standalone sensor units.

81. The system according to claim 74, wherein said QR and X-ray sensors are further adapted with sensors to automatically generate alarm signals to respectively identify QR and X-ray shielding present in said baggage.

82. The system according to claim 74, wherein said QR scanning is performed prior to said X-ray scanning.

83. The system according to claim 74, wherein said QR scanning is performed after said X-ray scanning.

84. The system according to claim 74, wherein said QR signals comprise RDX and PETN signals responsive to explosive compounds respectively containing RDX or PETN.

85. The system according to claim 74, wherein:

if said quadrupole resonance (QR) sensor triggers said QR system alarm or said indeterminate indication, then said X-ray sensor is further adapted to automatically, selectively generate bulk military alarm and clear signals to respectively identify the presence or absence of a default threshold amount of a bulk military class of explosives, wherein said default threshold amount identifies predetermined threat quantities of plastic and non-plastic types of explosives within said bulk military class of explosives; and wherein if said QR sensor triggers said QR clear indication, then said X-ray sensor is further adapted to automatically, selectively generate bulk military alarm and clear signals to respectively identify the presence or absence of a modified threshold amount of said bulk military class of explosives, wherein said modified threshold amount only identifies predetermined threat quantities of non-plastic types of explosives within said bulk military class of explosives.

86. A method for detecting explosives in baggage, said method comprising:

quadrupole resonance (QR) scanning said baggage using a QR sensor adapted to generate QR signals in response to explosive compounds containing QR responsive materials;

X-ray scanning said baggage for explosives using a X-ray sensor adapted to automatically, selectively generate alarm and clear signals to respectively identify the presence or absence of said explosives; and classifying said QR signals according to an alarm classification, said alarm classification comprising an QR alarm category indicating alarm resolution is required, a QR clear category indicating no sheet alarm resolution is required, and a QR indeterminate category defining QR signals which cannot be classified as being within said QR alarm category or said QR clear category.

87. The method according to claim 86, wherein:

if said QR signals are classified in said QR alarm category, then said baggage is identified as requiring said alarm resolution, even if said X-ray sensor generates a clear signal for sheet explosives resulting from said X-ray scanning; and wherein if said QR signals are classified in said QR clear category, then said baggage is identified as not requiring said sheet alarm resolution, even if said X-ray sensor generates an alarm for sheet explosives resulting from said X-ray scanning; and wherein if said QR signals are classified in said QR indeterminate category, then said method further comprises:

if said X-ray sensor generates a clear signal for sheet explosives resulting from said X-ray scanning, then said baggage is identified as not requiring said alarm resolution, subject to any other alarms generated by said X-ray sensor, otherwise, if said X-ray sensor generates an alarm signal for sheet explosives resulting from said X-ray scanning, then a sheet system alarm is triggered and said baggage is identified as requiring said alarm resolution.

* * * * *

UNITED STATES PATENT AND TRADEMARK OFFICE
CERTIFICATE OF CORRECTION

PATENT NO. : 6,922,460 B2
DATED : July 26, 2005
INVENTOR(S) : Skatter et al.

It is certified that error appears in the above-identified patent and that said Letters Patent is hereby corrected as shown below:

Title page,
Item [56], References Cited, OTHER PUBLICATIONS, insert
-- INVISION TECHNOLOGIES, CTX 5500 DS technical article, "CTX 5500: At Home in Busy Terminals," Invision Technologies, Newark, CA (June 2, 2003)
QUANTUM MAGNETICS, INC., QSCAN QR 500 technical specification, "Large Container Explosives Detection," Quantum Magnetics, Inc., San Diego, CA (June 2, 2003)
ED RAO, "Advanced Technology (AT) Explosive Detection Device Deployment in the Security Equipment Integrated Program," USA (1998) --.

Column 12,
Line 33, after "bag" delete "triggering5" and insert -- triggering --.

Signed and Sealed this

Third Day of January, 2006

JON W. DUDAS
*Director of the United States Patent and Trademark Office*